United States Patent
Atkinson (10) Patent No.: US 6,495,824 B1
(45) Date of Patent: Dec. 17, 2002

(54) ION MOBILITY SPECTROMETER, SPECTROMETER ANALYTE DETECTION AND IDENTIFICATION VERIFICATION SYSTEM, AND METHOD

(75) Inventor: David A. Atkinson, Idaho Falls, ID (US)

(73) Assignee: Bechtel BWXT Idaho, LLC, Idaho Falls, ID (US)

(*) Notice: Subject to any disclaimer, the term of this patent is extended or adjusted under 35 U.S.C. 154(b) by 0 days.

(21) Appl. No.: 09/524,323

(22) Filed: Mar. 13, 2000

(51) Int. Cl.[7] .................... B01D 59/44; H01J 49/00
(52) U.S. Cl. ................. 250/287; 250/281; 250/282
(58) Field of Search ........................ 250/281, 282, 250/287

(56) References Cited

U.S. PATENT DOCUMENTS

| | | | |
|---|---|---|---|
| 4,551,624 A | * 11/1985 | Spangler et al. | 250/287 |
| 4,797,554 A | * 1/1989 | Blanchard et al. | 250/287 |
| 4,855,595 A | * 8/1989 | Blanchard | 250/287 |
| 5,021,654 A | * 6/1991 | Campbell et al. | 250/287 |
| 5,095,206 A | * 3/1992 | Bacon, Jr. et al. | 250/282 |
| 5,491,337 A | * 2/1996 | Jenkins et al. | 250/287 |
| 5,736,739 A | * 4/1998 | Uber et al. | 250/287 |

* cited by examiner

Primary Examiner—John R. Lee
Assistant Examiner—David A. Vanore
(74) Attorney, Agent, or Firm—Wells StJohn Roberts Gregory & Matkin (57) ABSTRACT

Methods and apparatus for ion mobility spectrometry and analyte detection and identification verification system are disclosed. The apparatus is configured to be used in an ion mobility spectrometer and includes a plurality of reactant reservoirs configured to contain a plurality of reactants which can be reacted with the sample to form adducts having varying ion mobilities. A carrier fluid, such as air or nitrogen, is used to carry the sample into the spectrometer. The plurality of reactants are configured to be selectively added to the carrier stream by use inlet and outlet manifolds in communication with the reagent reservoirs, the reservoirs being selectively isolatable by valves. The invention further includes a spectrometer having the reagent system described. In the method, a first reactant is used with the sample. Following a positive result, a second reactant is used to determine whether a predicted response occurs. The occurrence of the second predicted response tends to verify the existence of a component of interest within the sample. A third reactant can also be used to provide further verification of the existence of a component of interest. A library can be established of known responses of compounds of interest with various reactants and the results of a specific multi-reactant survey of a sample can be compared against the library to determine whether a component detected in the sample is likely to be a specific component of interest.

10 Claims, 4 Drawing Sheets

ION MOBILITY SPECTROMETER, SPECTROMETER ANALYTE DETECTION AND IDENTIFICATION VERIFICATION SYSTEM, AND METHOD

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

FIELD OF THE INVENTION

This invention pertains to the field of spectrometry, and in particular to ion mobility spectrometry (IMS). In one aspect, the invention pertains to a method and apparatus for analyte detection and identification verification using spectrometry and, in particular, IMS.

BACKGROUND OF THE INVENTION

The term "ion mobility spectrometry" refers to the principles, practice and instrumentation for characterizing chemical substances through gas phase ion mobilities. In modern analytical IMS methods, ion mobilities are determined from ion velocities that are measured in a drift tube at ambient pressure (i.e., atmospheric pressure) with supporting electronics. Ion mobilities are characteristic of substances and can provide a means for detecting and identifying chemical compounds, or specific components of a sample. In practice, the sample is vaporized (if not already in a vapor state) and is then introduced into the reaction region of a drift tube where neutral molecules of the vapor undergo ionization. The resultant ions, i.e., product ions, are injected into the drift region for mobility analysis. Mobility is determined from the drift velocity attained by ions in a weak electric field. Although the mobility analysis described above occurs in a drift tube, other apparatuses can be utilized for mobility analyses. The term "spectrometry analyzer" is used herein to refer to a drift tube or other apparatus utilized for mobility analyses.

Ion velocities are inversely dependent on the effective collisional cross section of an ion and this makes IMS a type of molecular size analyzer. As the reactant ions and product ions are drawn towards and collide with the detector plate, current is registered and a signal is generated. The mobility spectrum represents the ion current intensity as a function of time. In instances where ions of several identities and different mobilities exist in the drift tube, ions can be separated through differences in mobilities. In order to provide greater separation between mobilities of different components in the sample, it is common to react the sample vapor with a reactant or reagent to alter the mobility of the molecules of interest to give greater separation between those molecules and other molecules which can exist in the sample.

In particular applications, molecules of interest are combined with chemicals to produce a much larger molecule having a much lower mobility in the drift tube. For example, RDX (cyclo-1,3,5-trimethylene-2,4,6-trinitramine) reacts particularly well with chloride to form a large molecule known as an adduct. The adduct, being of larger size, moves through the drift tube relatively slowly compared to other molecules which can exist in the sample and, therefore, the peak which identifies the RDX adduct is displayed later on a time log than are the peaks for RDX itself and other components. Reactions using reagents as described are particularly effective for those substances of interest which are polar in nature.

In summary, ion mobility spectrometry is comprised of, and governed by, two sequential processes. These are: A) gas phase ionization in air (or nitrogen) at atmospheric pressure through collisional charge exchange or ion-molecule reactions, and B) ion characterization using mobilities of gas phase ions in a weak electric field at ambient pressure (i.e., atmospheric pressure).

Ion mobility spectrometry has received a renewed interest in the last few years where only a decade ago the technique was regarded largely as a curiosity or an anachronistic technology within the ion-molecule chemistry and vapor sensing community. The resurgence of IMS instrumentation and technique is related to its intrinsic features of response (excellent detection limits) and to practical considerations (size, weight, and power advantages) when compared with well-established technologies such as mass spectrometry or gas chromatography/mass spectrometry.

While the use of IMS as a detection tool has experienced recent attention, elementary concepts in IMS are still relatively unrefined as compared to techniques such as mass spectrometry. For example, comprehensive models of response characteristics do not exist. Also, ion mobility spectrometry is an inherently low level resolution technique, and the low resolution of the ion mobility spectrometer can result in the overlapping of interferent peaks with the analyte peaks of interest. Specifically, an interferent peak can appear at the time when an analyte peak is expected, generating a false alarm as to the presence of the subject of interest.

Figure 1:
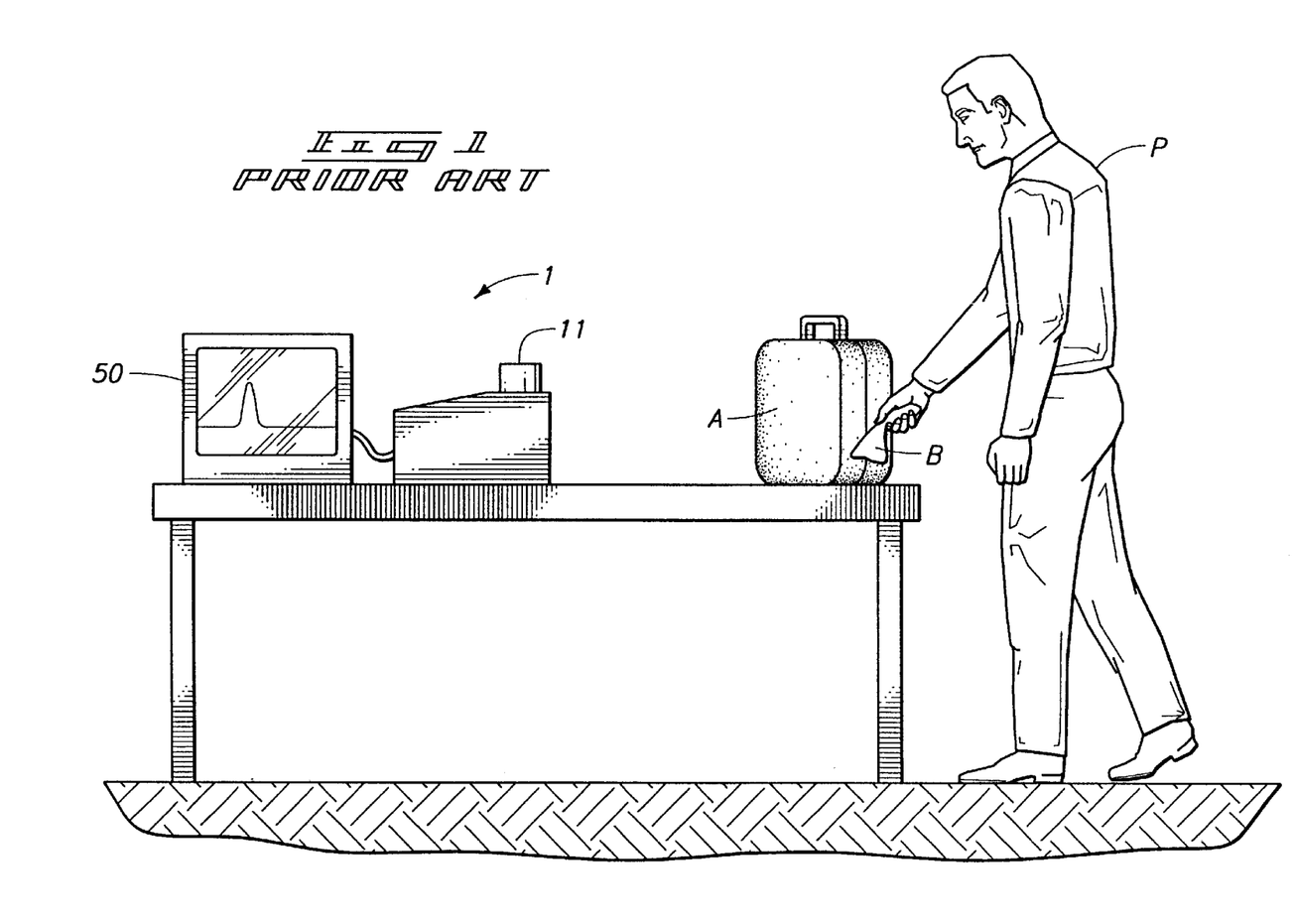
FIG. 1 is a prior art environmental view showing an ion mobility spectrometer as used in an airport security process.

One of the current uses for IMS is for the detection of contraband. FIG. 1 is an environmental view showing a typical IMS application in an airport security station which uses spectrometers of the prior art, but can also use a spectrometer containing the improvements of the present invention. In the example shown, the security officer "P" is checking for contraband which can be left on the outside of a handbag "A". The security officer will wipe the outer surface of the bag "A" with a small paper wipe "B". The paper wipe "B" is then inserted into a receptacle 11 in the ion mass spectrometer 1. Typically, air is drawn through a paper filter which is also heated, and any traces of particles from the surface of the handbag "A" which are picked up on the paper "B" will be drawn into the spectrometer 1. If the spectrometer detects the presence of potential contraband, such as, for example, RDX, TNT (trinitrotoluene), or PETN (pentaerythritol trinitrate), then the security officer will typically rerun the test. A second positive result may result in a manual search of the handbag. Given the delays in rerunning samples, as well as the inherent low resolution, it is desirable to have an ion mobility spectrometer which provides more certainty as to the accuracy of the results. Therefore, it is desirable to have an ion mobility spectrometer and ion mobility spectrometry methods which produce precise, accurate results.

SUMMARY OF THE INVENTION

Method and apparatus for improved detection and identification of components within a sample using spectrometry are disclosed.

In one aspect of the invention, a spectrometer comprises a sample inlet system configured to introduce a sample into a carrier fluid stream for transport of the sample within the spectrometer as a sample stream. A spectrometry analyzer is positioned downstream of the inlet system and is in fluid communication with the sample stream. The spectrometry analyzer produces signals in response to the chemical composition of components in the sample stream. A flow path is formed between the sample inlet system and the spectrometry analyzer. The spectrometer further comprises a signal processor configured to process the signals produced by the spectrometry analyzer to produce an outlet signal indicative of the presence of an identified substance. The spectrometer further comprises a reagent system configured to selectively introduce at least two reagents into the sample flow path. The reagent system comprises a first reagent reservoir and a second reagent reservoir in selective fluid communication with the sample flow path.

In another aspect of the invention, an ion mobility spectrometer analyte detection and identification verification system is disclosed. The system comprises a first reagent reservoir and a second reagent reservoir. The system further includes a carrier fluid inlet manifold having a sample inlet configured to receive the sample into the inlet manifold, a carrier fluid inlet connectable to a source of carrier fluid, and first and second carrier fluid outlets in respective fluid communication with the first and second reagent reservoirs. Additionally the system comprises an outlet manifold having first and second sample stream inlets in respective fluid communication with the first and second reagent reservoirs, and a sample stream outlet.

In yet another method, the invention encompasses a method for verifying the probable presence of a specific component in a sample. The method comprises the steps of providing a sample to be analyzed for the possible presence of a specific component, and providing a plurality of reactants known to form adducts with the specific component, the adducts having known ion mobilities. The method further comprises the steps of vaporizing and ionizing at least a part of the sample along with at least some of the reactants to create at least one vaporized, ionized analyte stream and then analyzing the analyte stream to determine the existence of components having the known ion mobilities. The existence of components having the known ion mobilities are indicative of the presence of the specific component.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Methods and apparatus for spectrometry detection and identification of components within a sample are disclosed. The methods are particularly useful in ion mobility spectrometry (IMS), but can also be used in other spectrometry applications, such as mass spectrometry. The apparatuses can comprise a spectrometer, specifically an ion mobility spectrometer, and can also comprise a spectrometer analyte detection and identification verification system which can be added to an existing spectrometer. More specifically, the spectrometer analyte detection and identification verification system can be connected to an existing ion mobility spectrometer.

In the examples described below, the methods and apparatuses will be described with particular application to ion mobility spectrometry, although it is understood that the methods can equally be applied to other methods of spectrometry.

In one aspect, an apparatus of the present invention comprises a spectrometer having a sample inlet system and an analyte detection system for analyzing at least part of the sample to identify specific components within the sample. A sample flow path is formed within the spectrometer between the sample inlet system and the analyzer. A reagent system is provided which is configured to provide to the sample flow path at least two reagents. This allows the sample to be reacted with two different reagents to form compounds, preferably adducts, which can then be analyzed to determine the presence or absence of a specific component within the sample. Preferably, the reagent system is configured to allow the reactants to be provided selectively. By providing different reactants, the arrival time of peaks as produced from the spectrometry analyzer can vary depending on the reactant and the compounds within the sample. Since it is possible to predetermine the reaction of compounds of interest with reactants of interest, it is possible to observe the effect that using different reactants will have on samples within the reactant. From known information about these effects and comparison with the actual results of the analysis, it is possible to determine the probable existence of certain components within the sample.

Various embodiments of the invention will now be described in detail.

Spectrometer Analyte Detection and Identification Verification System

Figure 2:
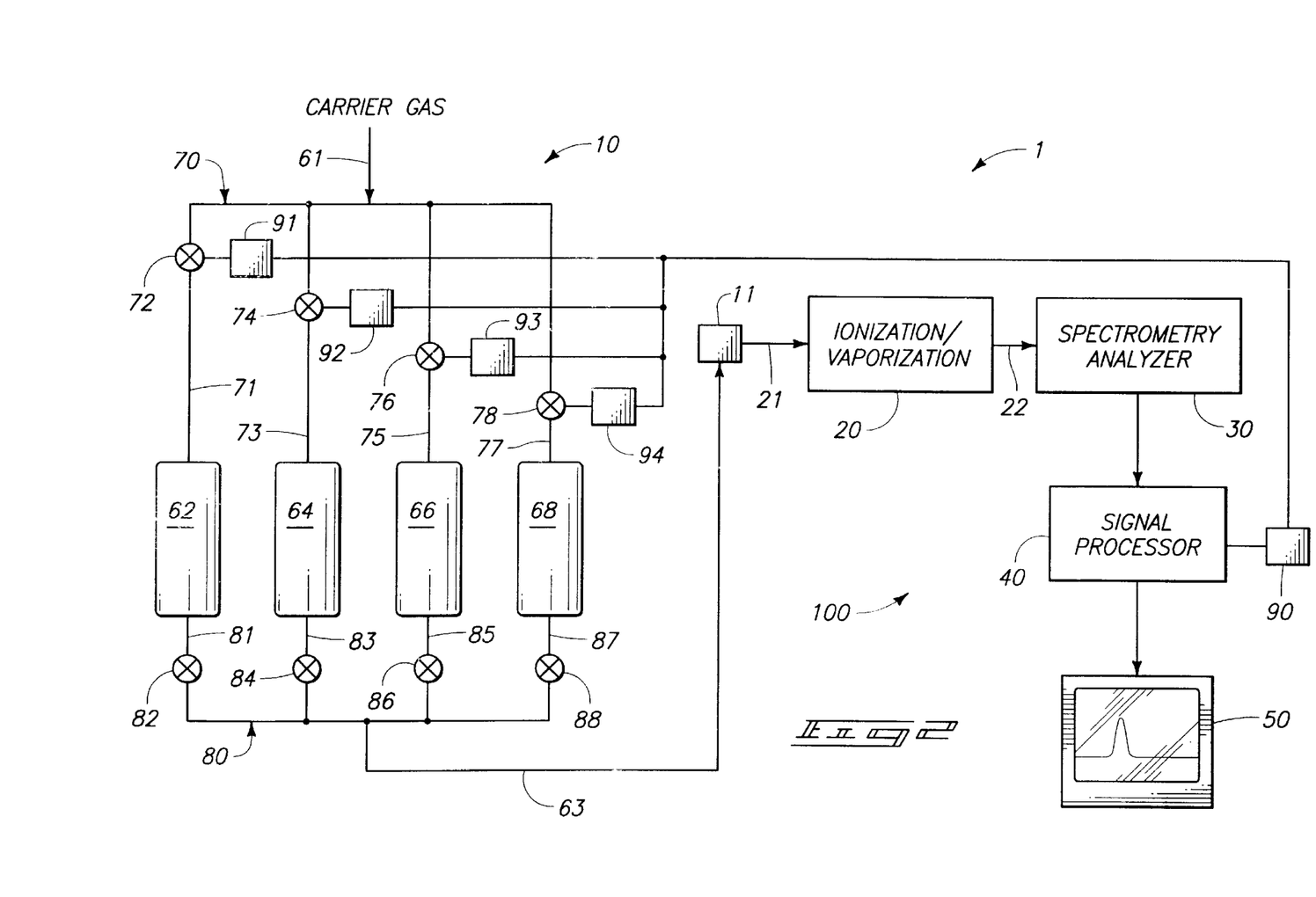
FIG. 2 is a schematic block diagram showing an analyte detection and identification verification system in an ion mobility spectrometer in accordance with the present invention.

Turning to FIG. 2, a spectrometer 100 is shown. The spectrometer, which is known in the art, includes a sample inlet 11, an ionization/vaporization system 20, a spectrometry analyzer 30, a signal processor 40, and an output device 50. The sample inlet system 11 can take various forms. In mass spectrometry, the sample inlet can be a hypodermic syringe used to inject a liquid sample into the spectrometer. In ion mobility spectrometry, the sample inlet system can consist of a holder for a paper filter which can be wiped on an article of interest to pick up samples for analysis, as shown in FIG. 1. In ion mobility spectrometry, a vacuum system can be employed to draw particles from the sample cloth "B" of FIG. 1 into the spectrometer. The sample is then vaporized and ionized, and the resulting analyte analyzed for specific components. As discussed previously, in order to improve the detectability of certain components with a sample it is known to react to the sample with a reactant such as chloride. In the normal configuration, the reactant is added to or is itself the carrier fluid used to carry the sample into the spectrometer.

A first embodiment of the invention is the spectrometer analyte detection and identification verification system 10 shown in FIG. 2. This system may also be known as the reagent system, due to the fact that reactants in the forms of reagents are provided to the sample by the system. In the spectrometer 100 of FIG. 2, between the sample inlet 11 and the spectrometry analyzer 30, there is formed a flow path which includes the sample inlet 11, the vaporization/ ionization unit 20, and any other conduit or flow chambers 21 and 22 between the sample inlet 11 and the spectrometry analyzer 30. The analyte detection and identification verification system is configured to provide a reagent to this flow path. In a preferred embodiment, the carrier gas provided at carrier gas inlet 61 can be selectively flowed through a plurality of reagent reservoirs 62, 64, 66 and 68, and thereafter provided to the spectrometer at the sample inlet 11 and, in this instance, act as the carrier fluid for the sample. In an alternate embodiment, the reagent can itself become the carrier fluid, although this is less preferable for a variety of reasons, including the need to dispose of the reagent. In alternate embodiments, the reagent can be provided at different points along the flow path.

In the preferred embodiment, the spectrometer analyte detection and identification verification system 10 of FIG. 2 comprises a carrier fluid inlet manifold 70 having a carrier fluid inlet 61. The fluid inlet 61 is connectable to a source of carrier fluid, and at least first and second carrier fluid outlets 71 and 73 in respective fluid communication with at least a first reagent reservoir 62 and a second reagent reservoir 64. The system further comprises an outlet manifold 80 having at least first and second reagent outlets 81 and 83 in respect to fluid communication with the first and second reagent reservoirs 62 and 64, and a sample stream outlet 63 configured to entrain a sample from sample inlet 11 into the sample stream.

Preferably, the carrier fluid from carrier fluid inlet 61 is in selective communication with the first and second reagent reservoir 62 and 64, and the reagent outlets 81 and 83 are in selective fluid communication with first and second reagent reservoirs 62 and 64. Such can be accomplished by valves 72 and 74 on the carrier fluid inlet manifold and valves 82 and 84 on the outlet manifold.

In an alternate embodiment, the spectrometer analyte detection and identification verification system 10 of FIG. 2 can be provided with a plurality of reagent reservoirs. In FIG. 2, an embodiment wherein four reagent reservoirs are used is shown. In the shown embodiment, the reagent reservoirs 62, 64, 66 and 68 are selectively connectable to the carrier fluid inlet line 61 as well as being selectively connectable to the sample stream outlet 63. Such is accomplished by valves 72, 74, 76 and 78 on the inlet manifold and valves 82, 84, 86 and 88 on the outlet manifold. Valves 72, 74, 76 and 78 are provided to prevent carrier gas from entering the reagent reservoir, and also to prevent the back flow of reagent into the inlet manifold and thence into the carrier gas. In this case, check valves can be used for valves 72, 74, 76 and 78. For the outlet valves on the outlet side of the reagent reservoirs, valves 82, 84, 86 and 88, solenoid valves are preferably employed to allow the reservoir to be selectively used or not used. Solenoid valves allow for the system to be automated so that the selection of reagents can be performed automatically.

The spectrometer analyte detection and identification verification system 10 of FIG. 2 can also be configured to inject the reagent at any other point in the spectrometer, if desirable, such as in the flow path 21 or flow path 22 between the sample inlet 11 and the spectrometry analyzer 30. However, in the preferred embodiment, the system provides the reagent as part of the carrier gas.

Reagent can be provided in the reagent reservoirs in various forms. In one embodiment, flow of a carrier gas over a permeation device provides the reagent. In a second embodiment, a liquid reagent head space in the flow path within the reagent reservoirs provides a vapor reagent to the carrier fluid. In a third embodiment, a head space is provided over a solid reagent in the reagent reservoirs to provide a vapor reagent. In a fourth embodiment, an impinger comprising gas flow through liquid reagent can be used to provide the reagent to the carrier gas. These examples are only for illustrative purposes and other embodiments of providing the reagent to the carrier gas can be employed. In yet another embodiment, the reagent gas can become the carrier fluid itself.

Spectrometer with Analyte Detection and Identification Verification System

A second embodiment of the invention comprises a spectrometer having the analyte detection and identification verification system described above. Such is shown in FIG. 2 as spectrometer 1 comprising traditional spectrometry components 100 as well as the reagent system 10. In the preferred embodiment, the reagent system 10 is connected to the sample inlet 11 and provides the carrier fluid which is used to entrain the sample and carry it through the spectrometer 100. As also described above, the reagent system can introduce the reagent at other points along the flow path of the sample such as flow path 21 between sample inlet 11 and the vaporization/ionization unit 20, as well as flow path 22 between the vaporization/ionization unit 20 and the spectrometry analyzer 30.

Preferably, the reagent system 10 selectively provides the reagents to the spectrometer by virtue of valves 82, 84, 86 and 88 on the outlet manifold 80, and valves 72, 74 76 and 78 on the carrier fluid inlet manifold 70. However, in certain embodiments, two reagents can be provided simultaneously, in which event the valves can optionally not be utilized to selectively isolate reagent reservoirs.

The spectrometer 1 can further comprise an identification verification system. The identification verification system 90 comprises a selective signal detection circuit configured to identify a first signal from the signal processor 40, the signal having a potential to be a signal of interest, the first signal being generated when a first reagent from the reagent system 10 is mixed with the sample stream. The selective signal detection circuit is further configured to identify a second signal from the signal processor 40, the second signal being generated when a second reagent from the reagent system 10 is mixed with the sample stream. A reagent switching circuit is configured to isolate the carrier fluid stream from the first reagent in the reagent system 10 and connect the sample stream to a second reagent in the reagent system. The isolating of the reagents from the carrier fluid can be accomplished by solenoid valves at valves 72–78 (even numbers) and solenoid actuators 91, 92, 93 and 94, respectively.

Using the identification verification system, it is possible to configure the spectrometer such that when a peak is detected using a first reagent, a second reagent can then be employed to check for an anticipated peak in the second location using the second reagent. As will be described further below, if the second peak is not found, then the first peak is not verified. In this way, the system can be configured such that the second reactant is only used, i.e., switched into the carrier gas stream by the reagent switching agent, when a first peak is detected which corresponds to a component of interest in the sample. The identification verification system can be further provided with a verification circuit configured to verify the probable presence of a specific component within the sample based on the existence of the first and second signals corresponding to use of the first and second reactants.

In an alternate embodiment, the reagent switching circuit can be configured to alternately isolate the sample stream from the first reagent in the reagent system and the connect the sample stream to a second reagent in the reagent system. Thereafter, the switching circuit isolates the sample stream from the second reagent in the reagent system and connects the sample stream to the first reagent in the reagent system. In this manner, if a substance of interest reacts with both reagents to produce recognizable peaks on the output display 50, a series of two oscillating peaks will appear, tending to verify the presence of the component of interest. Such switching from the first to the second reagent can be performed regardless of whether or not the first reagent produces a result. Such switching can be configured in a cyclic pattern to establish a set of oscillating peaks on the output display 50.

In yet another variation on the invention wherein the spectrometer further comprises the identification verification system 90, the reagent system 10 can further comprise a third reagent reservoir 66 which contains a third reagent. The third reagent reservoir 66 can be isolated selectively from the other reagents by valves 76 and 86, and can be automatically selected by solenoid operator 93. The signal detection circuit can be configured to identify a first anticipated response from the signal processor 40 in response to the third reagent from the reagent system being used in the sample stream. The anticipated response can be either the absence or the presence of a signal (peak) at a particular time. The verification circuit of the identification verification system 90 can be configured to verify the presence of a specific component within an analyzed material (referred to hereafter as the "analyte") based on the existence of first and second signals resulting from respective use of first and second reactants, in combination with either the existence of, or absence of, the first anticipated response from the third reactant. This concept will be described more fully below with respect to the detailed description of the method.

The reagent system 10 can further comprise a fourth reagent reservoir 68 in selective fluid communication with the sample stream outlet 63 via a fourth reagent outlet 87. It can be seen that an array of different reactants can be provided by connecting as many reagent reservoirs as are desired in parallel construction, as indicated in FIG. 2, and providing valves for isolation of the reservoir from the other reservoirs. In this manner, it is possible to improve the verification and identification of the existence of a component in the sample by looking for anticipated responses to the use of different reactants with the compound. Further it can be desirable to screen for a variety of components within the sample. Therefore, a variety of reactants can be utilized in order to produce a pattern of responses which provide a high probability for the existence of the range of anticipated components of interest. This method is more fully described below with respect to the method.

In yet another embodiment, the identification verification system can comprise a library of anticipated responses of various compounds to selected reagents. Such a library can be stored in digital form in the identification verification system 90. When a plurality of reagents are used on a specific sample, the actual responses obtained with the various reagents can be compared to the anticipated response from the library to identify the possible presence of a component in the analyte.

Method for Verifying the Probable Presence of a Specific Component in a Sample

The invention further comprises methods for verifying the probable presence of a specific component in a sample by use of a plurality of reagents with the sample. This provides additional data which can be analyzed to determine the probability that a response in the spectrometer is, in fact, generated by the component of interest within the sample.

Figure 3:
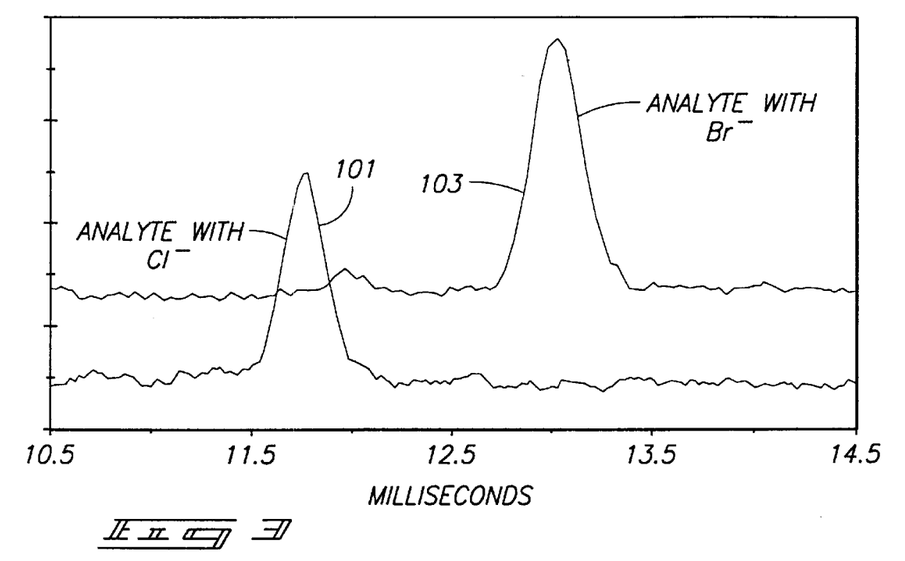
FIG. 3 is a graph showing the residence time of a sample of an analyte using two different reactants.

Turning to FIG. 3, an IMS output is shown. In this example, a sample containing an analyte was tested with two reactants, chloride ($Cl_-$) and bromide ($Br_-$). As can be seen, the analyte peak 101, when tested with a chloride reactant, appears at approximately 11.75 milliseconds, whereas the same component, when tested with bromide, appears at about 13 milliseconds as indicated by peak 103. Since such response times can be determined by testing components of interest with various reactants, it is possible to create a predictive output which can then be compared with an actual output to provide additional assurance that a first response is, in fact, a response due to the component of interest and not an interferent.

In the preferred embodiment, the sample stream is first reacted with a first reactant to determine whether a response indicative of a component of interest is found. If the first response occurs, then the sample stream is tested with a second reactant producing a known response with respect to the component of interest to determine whether the known response, in fact, occurs. Occurrence of the second response tends to verify the existence of the component of interest.

The method can also be practiced using more than one reactant with respect to the sample at the same time. In this case, the method comprises the steps of providing a sample to be analyzed for the possible presence of the specific component, and simultaneously providing a plurality of reactants known to form adducts with the specific component, the adducts having known ion mobilities. The sample is vaporized and ionized along with at least some of the reactants to create at least one vaporized/ionized analyte stream. The analyte stream is then analyzed to determine the existence of components having the known ion mobilities. When the existence of components having these known ion mobilities is found, it is indicative of the presence of the specific component within the sample.

Figure 4:
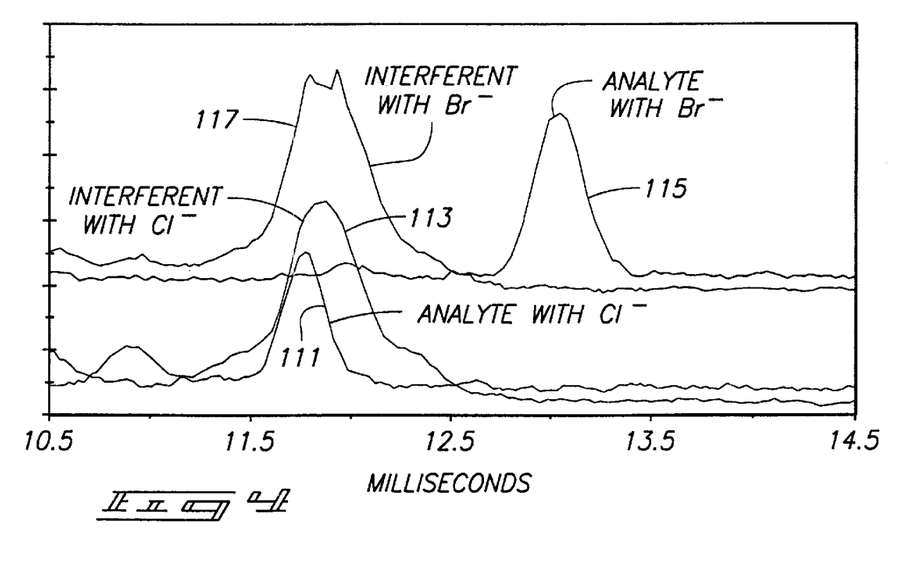
FIG. 4 is a graph showing how the response peak of a chemical can be obscured by an interferent peak and how the response peak of the chemical of interest can be moved away from the interferent peak by use of a different reactant.

With respect to FIG. 4, the lower two traces show how a component of interest can be hidden by an interferent. Interferent line 113 appears at about the same time as the peak 111, which is produced at about 11.75 milliseconds when the analyte reacts with chloride. However, an operator will not know whether the peak at 11.75 milliseconds is due to the analyte or the interferent. If it is known that the analyte, when reacted with bromide, produces a peak at about 13 milliseconds, then the sample can be further reacted with bromide to determine whether a peak indicative of the actual presence of the analyte appears at about 13 milliseconds. As is seen, the peak 115 tends to verify the existence of the analyte and separates the analyte peak from the interferent peak 117. The absence of a peak at approximately 13 milliseconds would leave only the interferent peak 117, indicating that the peak detected using chloride at about 11.75 milliseconds was merely an interferent peak and not a peak due to a material of interest.

Figure 5:
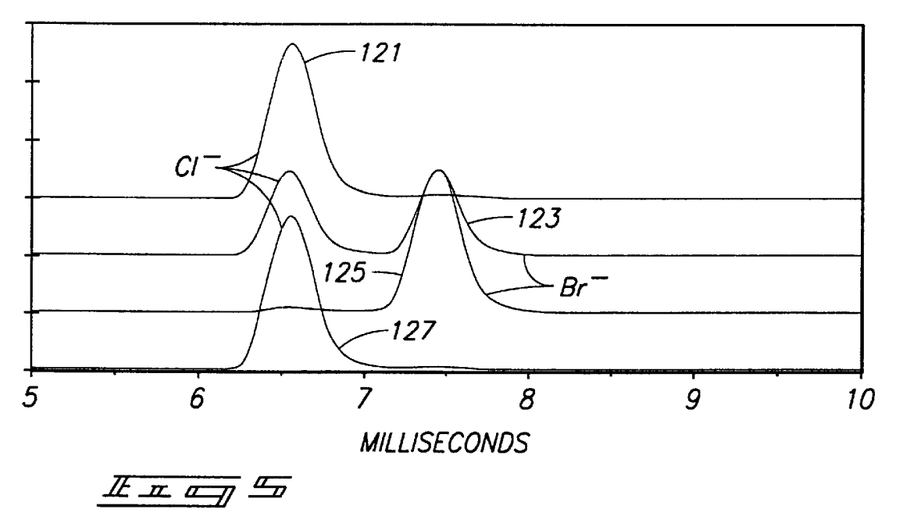
FIG. 5 is a graph showing the response of a peak of a certain chemical to a change in reactant from a first reactant to a second reactant and back to the first reactant.

In a variation on the above-described first embodiment method of the invention, the two reactants can be used in all cases rather than only using the second reactant when a response is obtained using the first reactant. In such variation, the first and second reactants can be used in an continuously alternating manner. For example, turning to FIG. 5, an exemplary chart is shown wherein a compound of interest produces a peak 121 with chloride at about 6.5 milliseconds and a peak 125 with bromide at about 7.5 milliseconds. As the sample is reacted first with chloride, peak 121 occurs first in a sequence of peaks. The chloride is then isolated from the system and bromide is introduced to the sample. For a short time, both chloride and bromide will be present in the system, providing small peaks 122 and 123 at approximately 6.5 milliseconds and 7.5 milliseconds, respectively, in a second sequence of peaks. After a short period of time, the system will be using only a bromide reactant and only the peak 125 at 7.5 milliseconds will occur as shown in a third sequence of peaks. Thereafter, the system is switched back to chloride and the peak 127 at approximately 6.5 milliseconds reappears. Therefore, by alternately switching between components, a wave pattern such as that shown in FIG. 5 can be established and displayed on a display output of a spectrometer. By very rapid switching, a pattern similar to that as shown in FIG. 3 can be produced. If it is known that, for example, the analyte produces peaks at 11.75 milliseconds with chloride and at 13 milliseconds with bromide, as indicated in FIG. 3, then the displayed pattern of the two peaks of FIG. 3 tends to indicate the presence of the analyte within the sample.

In a second embodiment of the methods of the invention, a third reactant is used within the system. The third reactant can be selected such that the reactant produces a peak when combined with the component of interest or, alternately, produces no peak when combined with the component of interest. This information, the existence or absence of a peak, can be used to verify the presence of a component. For example, with respect to FIG. 3, there can be more than one substance which produces peaks at 11.75 milliseconds and 13 milliseconds when reacted with chloride and bromide, respectively. However, only one of these two substances may produce a third peak when reacted with iodide. In this instance, the appearance of a third peak at a known response time when reacted with iodide would verify that the component detected was one or the other of the two possible components. Alternately, if a substance of non-interest produces a peak when reacted with iodide, whereas a substance of interest produces no peak when reacted with iodide, the absence of a peak when iodide is used as a reactant tends to verify the existence of the substance.

Therefore, given a universe of compounds of interest as well as a universe of potential interferents, it is possible to develop a library of spectrometry results which can be compared against actual results to verify the probable existence or absence of a compound of interest. Such is accomplished by taking a sample of a compound of interest and reacting it with various reactants and subjecting the resulting analytes individually to a spectrometry analyzer to determine the response of the analyzer to the reactant sample. In formulating strategies for developing such a library of anticipated results, reactants are selected, preferably on their ability to form an adduct with the compound of interest as the formation of adducts tends to produce larger separations of peaks between components. Distinct patterns of peaks can be used to positively identify a component of interest. When similar outputs are produced using specific reactants, further reactants can be used with the sample to attempt to produce a unique response pattern for a component of interest. As discussed above, a lack of a response of one component with one reactant as compared to a response of another component with the same reactant can be useful information in classifying the compound.

In compliance with the statute, the invention has been described in language more or less specific as to structural and methodical features. It is to be understood, however, that the invention is not limited to the specific features shown and described, since the means herein disclosed comprise preferred forms of putting the invention into effect. Therefore, the invention is claimed in any of its forms or modifications within the proper scope of the appended claims appropriately interpreted in accordance with the doctrine of equivalents.

I claim:

1. An ion mobility spectrometer comprising:
   a sample inlet system configured to receive a sample for introduction into a carrier fluid stream for transport of the sample within the spectrometer as a sample stream;
   a sample vaporization and ionization system in fluid communication with the sample stream, configured to vaporize and ionize at least a part of the sample to produce analyte in an analyte stream;
   a spectrometry analyzer positioned downstream of the sample vaporization and ionization system and in fluid communication with the analyte stream, the spectrometry analyzer producing signals in response to the chemical composition of the analyte;
   a signal processor configured to process the signals produced by the spectrometry analyzer to produce an output signal indicative of the presence of identified substances;
   a reagent system configured to introduce a plurality of reagents into the carrier fluid, the reagent system comprising:
      a first reagent reservoir;
      a second reagent reservoir;
      a carrier fluid inlet manifold having a carrier fluid inlet connectable to a source of carrier fluid, and first and second carrier fluid outlets in respective fluid communication with the first and second reagent reservoirs, the carrier fluid inlet of the carrier fluid inlet manifold being in selective fluid communication with the first and second reagent reservoirs; and
      an outlet manifold having first and second reagent outlets in respective fluid communication with the first and second reagent reservoirs, and a sample stream outlet configured to entrain a sample from the sample inlet system into the sample stream, the sample stream outlet being in selective fluid communication with the first and second reagent reservoirs; wherein the selective fluid communication of the carrier fluid inlet, and the selective fluid communication of the first and second reagent reservoirs with the sample stream outlet, is achieved using valves; and an identification verification system, comprising:
      a selective signal detection circuit configured to identify a first signal from the signal processor having a potential to be a signal of interest, the first signal being generated when a first reagent from the reagent system is mixed with the sample stream, the selective signal detection circuit being further configured to identify a second signal from the signal processor, the second signal being generated when a second reagent from the reagent system is mixed with the sample stream; and a reagent switching circuit configured to isolate the carrier fluid stream from the first reagent in the reagent system and connect the sample stream to a second reagent in the reagent system.

2. The ion mobility spectrometer of claim 1 wherein the valves comprise automatically operable solenoid valves.

3. The ion mobility spectrometer of claim 2 wherein in the reagent switching circuit is configured to isolate the sample stream from the first reagent in the reagent system and connect the sample stream to a second reagent in the reagent system in response to identification of the first signal by the signal detection circuit.

4. The ion mobility spectrometer of claim 3 further comprising a verification circuit configured to verify the probable presence of a specific component within the analyte based on the existence of the first and second signals.

5. The ion mobility spectrometer of claim 2 wherein the reagent switching circuit is configured to alternately isolate the sample stream from the first reagent in the reagent system and connect the sample stream to a second reagent in the reagent system, and isolate the sample stream from the second reagent in the reagent system and connect the sample stream to the first reagent in the reagent system.

6. The ion mobility spectrometer of claim 4 wherein:

the reagent system further comprises a third reagent reservoir in selective fluid communication with the sample stream outlet via a third reagent outlet;

the signal detection circuit is configured to identify a first anticipated response from the signal processor, the first anticipated response being generated when a third reagent from the reagent system is included in the sample stream; and the verification circuit is configured to verify the presence of the specific component within the analyte based on the existence of the first and second signals in combination with one of the existence or absence of the first anticipated response.

7. The ion mobility spectrometer of claim 6 wherein the verification circuit further comprises a library of anticipated first and second signals and first responses which are correlated to at least one component which may be present in the analyte, and wherein the circuit is further configured to compare actual first and second signals and first responses against the library to identify the possible presence of the component in the analyte.

8. The ion mobility spectrometer of claim 6 wherein:

the reagent system further comprises a fourth reagent reservoir in selective fluid communication with the sample stream outlet via a third reagent outlet;

the signal detection circuit is configured to identify a second anticipated response from the signal processor, the second anticipated response being generated when a fourth reagent from the reagent system is included in the sample stream; and the verification circuit is configured to verify the presence of the specific component within the analyte based on the existence of the first and second signals in combination with a predetermined combination of the existence or absence of the first anticipated response and the existence or absence of the second anticipated response.

9. The ion mobility spectrometer of claim 8 wherein:

the reagent system further comprises a fifth reagent reservoir in selective fluid communication with the sample stream outlet via a third reagent outlet;

the signal detection circuit is configured to identify a third anticipated response from the signal processor, the third anticipated response being generated when a fifth reagent from the reagent system is included in the sample stream; and the verification circuit is configured to verify the presence of the specific component within the analyte based on the existence of the first and second signals in combination with a predetermined combination of the existence or absence of the first anticipated response, the existence or absence of the second anticipated response, and the existence or absence of the second anticipated response.

10. A spectrometer comprising:

a sample inlet system configured to introduce a sample into a carrier fluid stream for transport of the sample within the spectrometer as a sample stream;

a spectrometry analyzer positioned downstream of the inlet system and in fluid communication with the sample stream, the spectrometry analyzer producing signals in response to the chemical composition of components in the sample stream;

wherein a sample flow path is formed between the sample inlet system and the spectrometry analyzer, the spectrometer further comprising;

a signal processor configured to process the signals produced by the spectrometry analyzer to produce an output signal indicative of the presence of identified substances;

a reagent system configured to selectively introduce at least two reagents into the sample flow path, the reagent system comprising a first reagent reservoir and a second reagent reservoir in selective fluid communication with the sample flow path; and a reagent switching circuit configured to control the selective fluid communication of the first reagent reservoir and the second reagent reservoir with the sample flow path in response to the output signal.

* * * * *